(12) United States Patent
Kalkbrenner et al.

(10) Patent No.: US 9,091,653 B2
(45) Date of Patent: Jul. 28, 2015

(54) MICROSCOPE AND METHOD FOR WAVELENGTH-SELECTIVE AND HIGH SPATIAL RESOLVING MICROSCOPY

(71) Applicant: Carl Zeiss Microscopy GmbH, Jena (DE)

(72) Inventors: Thomas Kalkbrenner, Jena (DE); Ralf Wolleschensky, Jena (DE)

(73) Assignee: Carl Zeiss Microscopy GmbH, Jena (DE)

( * ) Notice: Subject to any disclaimer, the term of this patent is extended or adjusted under 35 U.S.C. 154(b) by 365 days.

(21) Appl. No.: 13/754,679

(22) Filed: Jan. 30, 2013

(65) Prior Publication Data

US 2013/0222567 A1    Aug. 29, 2013

(30) Foreign Application Priority Data

Jan. 30, 2012    (DE) .......................... 10 2012 201 286

(51) Int. Cl.
*H04N 9/47*        (2006.01)
*H04N 7/18*        (2006.01)
(Continued)

(52) U.S. Cl.
CPC ............ *G01N 21/64* (2013.01); *G01N 21/6458* (2013.01); *G02B 21/16* (2013.01); *G02B 21/365* (2013.01); *G02B 27/58* (2013.01)

(58) Field of Classification Search
USPC .............. 348/79, 65, 54, 49, 46, 208.15, 326, 348/333.04, 333.11, 382, 756, 779, 781, 348/811; 250/216, 227.18, 309, 311, 368, 250/458.1, 459.1, 559.14; 359/362, 368, 359/370, 382, 385, 388, 390, 656; 356/363, 356/368
See application file for complete search history.

(56) References Cited

U.S. PATENT DOCUMENTS

2003/0139886 A1*  7/2003  Bodzin et al. ................... 702/28
2004/0061932 A1*  4/2004  Pensel et al. ................. 359/368
(Continued)

FOREIGN PATENT DOCUMENTS

DE    10 2006 021317 B3    10/2007
DE    20 2006 021317 B3    10/2007
(Continued)

OTHER PUBLICATIONS

Srinivasan et al.; Optical Engineering, Nov. 2009; vol. 48; Micro-Optical Spatial and Spectral Elements; 3 pages.
(Continued)

*Primary Examiner* — Jefferey Harold
*Assistant Examiner* — Mustafizur Rahman
(74) *Attorney, Agent, or Firm* — Patterson Thuente Pedersen, P.A.

(57) ABSTRACT

A method for wavelength-selective and high spatial resolving fluorescence microscopy. In a specimen fluorescence emitters are repeatedly excited and specimen frames are produced with a microscope. The fluorescence emitters are excited to emit fluorescence radiation such that at least a sub-set is isolated in each frame and the positions of the isolated fluorescence emitters are localized with a localization precision exceeding the optical resolution and a high-resolution complete image is produced. The imaging beam path of the microscope has a spectrally selective element which, during production of the frames, generates a spectrally-dependent rotational asymmetric point-spread function, such that images of isolated fluorescence emitters have a rotational asymmetry which depends on a wavelength at which the isolated fluorescence emitters fluoresce, and the images of the isolated fluorescence emitters are analyzed with respect to rotational asymmetry and an indication of the wavelength of the isolated fluorescence emitters is derived therefrom.

18 Claims, 3 Drawing Sheets

(51) Int. Cl.
*G01N 21/64* (2006.01)
*G02B 21/16* (2006.01)
*G02B 21/36* (2006.01)
*G02B 27/58* (2006.01)

(56) References Cited

U.S. PATENT DOCUMENTS

| | | | |
|---|---|---|---|
| 2005/0111088 A1* | 5/2005 | Winterot et al. | 359/368 |
| 2005/0185274 A1* | 8/2005 | Geier et al. | 359/462 |
| 2005/0237605 A1* | 10/2005 | Vodyanoy et al. | 359/385 |
| 2006/0192115 A1* | 8/2006 | Thomas et al. | 250/306 |
| 2007/0165221 A1* | 7/2007 | Deck et al. | 356/326 |
| 2009/0059360 A1 | 3/2009 | Evans et al. | |
| 2009/0263002 A1 | 10/2009 | Cremer et al. | |
| 2009/0279169 A1* | 11/2009 | Hoult et al. | 359/385 |
| 2010/0134605 A1* | 6/2010 | Demos et al. | 348/65 |
| 2010/0321686 A1 | 12/2010 | Correns et al. | |
| 2011/0102787 A1 | 5/2011 | Hess et al. | |
| 2011/0122488 A1* | 5/2011 | Truong et al. | 359/385 |
| 2011/0160083 A1 | 6/2011 | Hell et al. | |
| 2011/0174986 A1 | 7/2011 | Kempe et al. | |
| 2011/0226965 A1 | 9/2011 | Wolleschensky et al. | |
| 2012/0224034 A1 | 9/2012 | Kalkbrenner et al. | |

FOREIGN PATENT DOCUMENTS

| | | |
|---|---|---|
| DE | 10 2008 049 886 A1 | 4/2010 |
| DE | 10 2008 059 328 A1 | 6/2010 |
| DE | 10 2009 030 468 A1 | 1/2011 |
| DE | 10 2009 043 744 A1 | 3/2011 |
| WO | WO 2006/127692 A2 | 11/2006 |
| WO | WO 2012/039636 A2 | 3/2012 |

OTHER PUBLICATIONS

Heilemann et al.; Laser & Photon. Rev. 3, No. 1-2, pp. 180-202; Photoswitches: Key Molecules for Subdiffraction-Resolution Fluorescence Imaging and Molecular Quantification; 23 pages, Sep. 15, 2005.

Lukyanov et al.; Nature Reviews; Molecular Cell Biology; vol. 6, Nov. 2005; Photoactivatable Fluorescent Proteins; 7 pages.

* cited by examiner

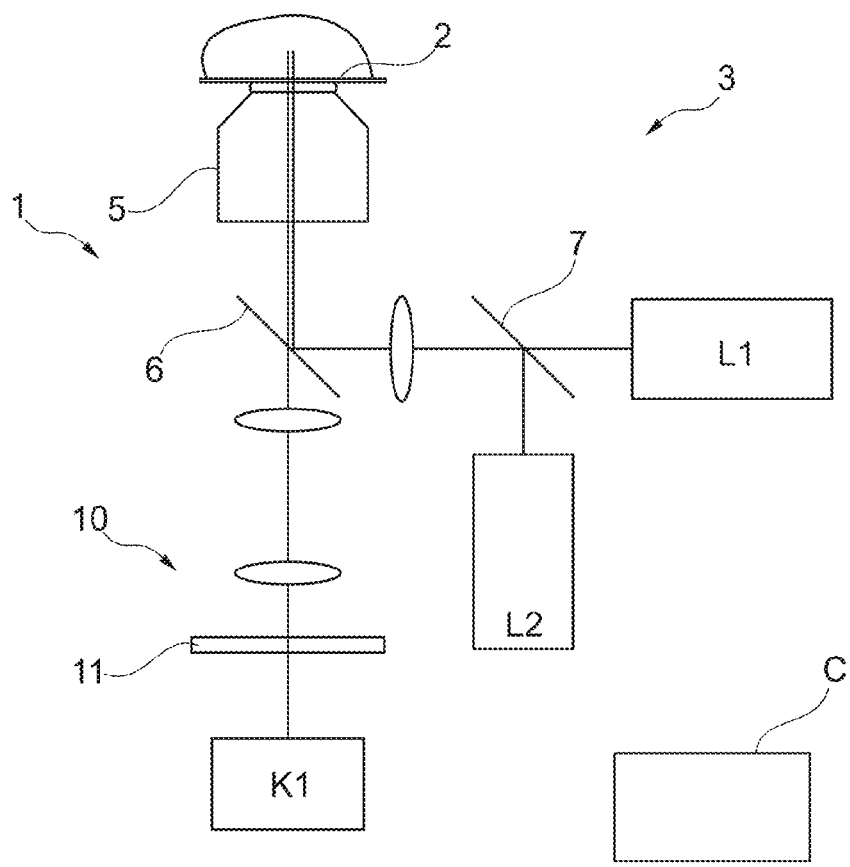
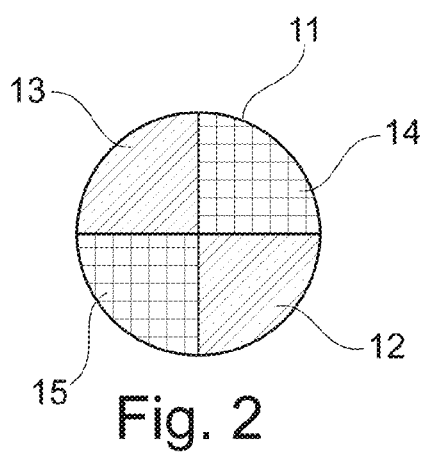
Fig. 2
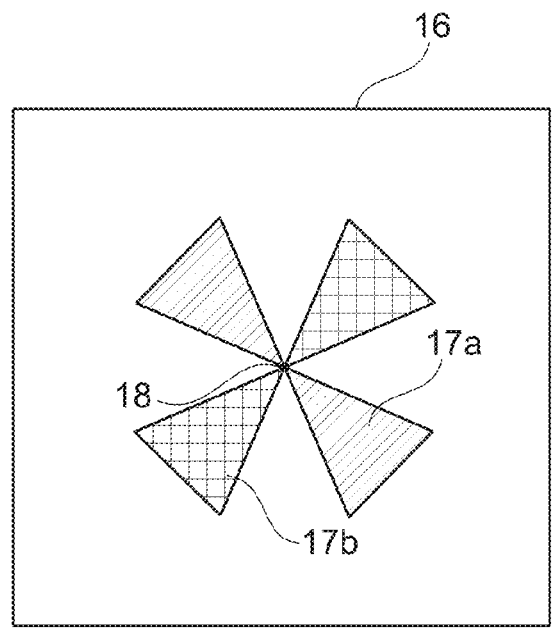
Fig. 3

Content beginning …

MICROSCOPE AND METHOD FOR WAVELENGTH-SELECTIVE AND HIGH SPATIAL RESOLVING MICROSCOPY

PRIORITY CLAIM

The present application claims priority to DE application no. 102012201286.9, filed Jan. 30, 2012, entitled MICROSCOPE AND METHOD FOR WAVELENGTH-SELECTIVE AND HIGH SPATIAL RESOLVING MICROSCOPY, which is incorporated by reference herein in its entirety.

BACKGROUND OF THE INVENTION

Various methods of braking the diffraction limit in microscopy have been developed in the state of the art. A method abbreviated to PALM (photo activated light microscopy) is known from WO 2006/127692 or DE 102006021317 A1, which uses a label substance for imaging a specimen which can be activated e.g. by means of optical radiation. Only in the activated state can the label substance emit specific fluorescence radiation. Non-activated molecules of the label substance emit no, or at least no noticeable, fluorescence radiation even after irradiation by excitation radiation. The activation radiation is therefore generally called a switching signal. In the PALM method, the switching signal is applied such that at least some of the activated label molecules are spaced apart from neighbouring activated molecules such that these label molecules are isolated, as measured by the optical resolution of the microscopy, or can be isolated subsequently by image processing methods. It is said that a sub-set of isolated fluorescence emitters is formed. After recording the fluorescence radiation, for these isolated emitters the centre of their radiation distribution is then identified, which distribution is a result, of the limited optical resolution. Doing this, the position of the molecules can be determined computationally with higher precision than the optical resolution itself allows. This procedure is called localization. The increased resolution so by computational determination of the centre of the diffraction distribution is also called "superresolution" in the technical literature. It requires that in the specimen at least a sub-set of the activated label molecules is distinguishable with the optical resolution, i.e. consists of isolated emitters. Their position can be determined with higher precision, then; they can be localized.

To isolate individual label molecules, the PALM principle utilizes statistical effects. In the case of a label molecule which can be excited to fluorescence radiation after receiving the switching signal of given intensity, it can be ensured, by adjusting the intensity of the switching signal, that the probability of activating label molecules present in a given area of the specimen is so small that there are enough sub-sections in which only label molecules emit fluorescence radiation which molecules are distinguishable within the optical resolution.

The PALM principle was refined with respect to the activation of the molecules to be detected. Thus for example, in the case of molecules that have as long-living non-fluorescing and a short-living fluorescing state, a separate activation needing activation radiation differing spectrally from the excitation radiation is not necessary. Instead the specimen is first activated with high-intensity illumination radiation such that the vast majority of the molecules is converted to the long-living state (e.g. a triplet state) in which they cannot fluoresce. The remaining, still fluorescing molecules are thereby isolated in respect of the optical resolution.

It may also be noted that the PALM principle has meanwhile also acquired other abbreviations, such as for example STORM, in the technical literature. In this description, the abbreviation PALM is used for all microscopy imagings which achieve a spatial resolution beyond the optical resolution of the apparatus used by first isolating and then localizing fluorescence molecules. The PALM method has the advantage that no high spatial resolution is required for the illumination. A simple widefield illumination is possible.

The PALM principle requires many frames of the specimen to be recorded, each of which contains a sub-set of isolated molecules. In order to image the specimen completely, the quantity of all frames must ensure that if possible all molecules were contained at least once in a sub-set. The PALM method therefore usually requires a large number of frames, which means that it takes a certain period of time to record a complete image. This is associated with a considerable computational outlay as a large number of molecules must be computationally localized in each frame. Large amounts of data are accumulated.

There is now a need not only to record high-resolution images in is colour channel, but to obtain colour information, i.e. an indication of the wavelength of the fluorescing emitters. In fluorescence microscopy, the state of the an knows a microscope according to FIG. 8. The fluorescence microscope 100 shown there comprises an illumination beam path 3 as well as an imaging beam path 4 which illuminate a specimen 2 with excitation radiation via a common objective 5 and image the fluorescing specimen 2. The illumination beam path 3 is combined with the imaging beam path 4 via a beam splitter 6, usually dichroic, such that illumination radiation from the illumination beam path 3 is incident on the specimen 2 through the objective 5 as well as the imaging of the specimen is carried out through the objective 5 and via the imaging beam path 4. The illumination beam path 3 usually has several spectral channels; in the representation in FIG. 8 two laser sources L1 and L2 are shown by way of example, the radiation of which is combined via a beam splitter 5. The illumination beam path 3 thus illuminates the specimen 2 with radiation of at least two wavelengths, with the result that a multicoloured excitation of the specimen 2 to fluorescence radiation is effected. The specimen 2 also emits multicoloured fluorescence radiation (naturally this could also be the case for as monochrome fluorescence excitation and different fluorescence molecules). In the imaging beam path 4, the image of the specimen 2 is therefore divided onto three colour channels, i.e. directed to three cameras K1, K2 and K3, via two beam splitters 8 and 9 as well as suitable lens systems not described in more detail. The splitting via the beam splitters 8 and 9 effects a spectrally selective split to the cameras K1 to K3. Alternatively or in addition, suitable colour filters can be used. Several colour channels are thus obtained, one for each camera. However, a disadvantage of this design is that the camera systems used are very expensive due to the high resolution required. Furthermore, the installation space for the microscope 100 is large on account of the required beam paths and colour splitters. The cameras are also usually cooled and likewise require a large installation space, further problem is that the cameras K1, K2 and K3 must be aligned precisely relative to one another so that the images of the individual colour channels are subsequently positioned correctly relative to one another. Any alignment error between the beam paths of the individual colour channels would result in a colour aberration constituting a chromatic aberration in the complete image.

It would be conceivable to use the microscope 100 of FIG. 8 for the PALM principle, but then the amount of data accumulating as well as the computational outlay would be multiplied by the number of colour channels.

SUMMARY OF THE INVENTION

The invention relates to a method for wavelength-selective and high spatial revolving fluorescence microscopy, wherein in a specimen fluorescence emitters are repeatedly excited to emit fluorescence radiation and frames of the specimen are produced with a microscope having an imaging beam path with an optical resolution, wherein the fluorescence emitters are excited to emit fluorescence radiation such that at least a sub-set of the fluorescence emitters is isolated in each frame, the positions of the isolated fluorescence emitters are localized with a localization precision exceeding the optical resolution in the produced frames and a high-resolution complete image is produced therefrom.

The invention further relates to a fluorescence microscope for wavelength-selective imaging of a specimen with a spatial resolution better than an optical resolution, which microscope has an illumination device which is designed to repeatedly excite fluorescence emitters to emit fluorescence radiation in the specimen, an imaging device comprising an imaging beam path with the optical resolution, which imaging device is designed to produce frames of the specimen with the optical resolution, a control device which is designed to control the illumination device and the imaging device such that several frames of the specimen are produced, wherein the fluorescence emitters are excited to emit fluorescence radiation such that at least a sub-set of the fluorescence emitters is isolated in each frame, wherein the control device is designed to localize the positions of the isolated fluorescence emitters with a localization precision exceeding the optical resolution in the produced frames and to produce a high-resolution complete image therefrom.

A feature and advantage of embodiments of the invention is therefore to provide a microscope as well as a method for wavelength-selective, high-resolution fluorescence microscopy which avoids the described disadvantages of the state of the art. In particular, size and range of parts, alignment outlay and amount of data are to be reduced.

This feature and advantage is achieved according to the invention with a method for wavelength-selective and high spatial resolution fluorescence microscopy, wherein in a specimen fluorescence emitters are repeatedly excited to emit fluorescence radiation and frames of the specimen are produced with a microscope having an imaging beam path with an optical resolution, wherein the fluorescence emitters are excited to emit fluorescence radiation such that at least a sub-set of the fluorescence emitters is isolated in each frame, the positions of the isolated, fluorescence emitters are localized in the produced frames with a localization precision exceeding the optical resolution, and a high-resolution complete image is produced therefrom, the imaging beam path of the microscope has a spectrally selective element which, during the production of the frames, generates a spectrally-dependent rotational asymmetric point-spread function, with the result that images of isolated fluorescence emitters have a rotational asymmetry which depends on a wavelength at which the isolated fluorescence emitters fluoresce, and in the frames the images of the isolated fluorescence emitters are analysed in respect of rotational asymmetry and an indication of the wavelength of the isolated fluorescence emitters is derived therefrom.

These feature and advantages are further achieved with a fluorescence microscope for wavelength-selective imaging of a specimen with a spatial resolution increased compared with an optical resolution, which microscope comprises an illumination device which is designed to repeatedly excite fluorescence emitters to emit fluorescence radiation in the specimen, an imaging device comprising an imaging beam path, which is designed to produce frames of the specimen with the optical resolution, a control device which is designed to control the illumination device and the imaging device such that several frames of the specimen are produced, wherein the fluorescence emitters are excited to emit fluorescence radiation such that at least a sub-set of the fluorescence emitters is isolated in each frame, wherein the control device is designed to localize the positions of the isolated fluorescence emitters with a localization precision exceeding the optical resolution in the produced frames and to produce a high-resolution complete image therefrom, the imaging beam path of the microscope has a spectrally selective element which, during the production of the frames, generates a spectrally-dependent rotational asymmetric point-spread function, with the result that the images of isolated fluorescence emitters have a rotational asymmetry which depends on a wavelength at which the isolated fluorescence emitters fluoresce, and the control device is designed to analyse in the frames the images of the isolated fluorescence emitters with respect to rotational asymmetry and to derive therefrom an indication of the wavelength of the isolated fluorescence emitters.

The limitation, present in the state of the art, of multicoloured widefield detection for high resolution is overcome according to the invention by encoding the spectral information of the emitters in a rotational asymmetry of the point-spread function and thus ultimately in their appearance on the camera. This is carried out by using the spectrally selective element in the imaging beam path which element gives the point-spread function a spectrally dependent rotationally asymmetric form. In contrast to conventional fluorescence microscopy, this approach is possible for the localization-based high resolution microscopy according to the PALM principle as the PALM principle deals with individual molecules per se on the basis of isolation and localization. The disturbance in the point-spread function, thus otherwise strictly to be avoided in normal microscopy, thus surprisingly leads to the advantage of a simple wavelength selection for the PALM principle.

In the frames, the images of the isolated fluorescence emitters are analysed with respect to rotational asymmetry. The wavelength of the detected radiation can easily be ascertained from as determined, rotational asymmetry as the spectrally dependent rotational symmentry disturbance introduced by the spectrally selective element is known.

The term "image of a fluorescence emitter" means the generally diffraction-limited point image.

One can particularly easily analyse the rotational asymmetry by determining an angle indication of the image for each image of one of the isolated fluorescence emitters. The angle indication then provides the indication of the wavelength of the isolated fluorescence emitter, as the spectrally selective element converts individual wavelengths to different angular positions of the rotational asymmetry.

The method can be carried out particularly easily if the spectrally selective element generates a point-symmetric rotational asymmetric point-spread function. The rotationally asymmetric images of the individual fluorescence emitters then differ only in the rotation position which depends on the colour, i.e. the wavelength of the individual fluorescence emitter. It is then relatively easily possible to derive the indication of the wavelength of the isolated fluorescence emitters by determining the rotational position for each image of one of the isolated fluorescence emitters.

A point-symmetric rotational asymmetry further has the advantage that the location can be easily determined wavelength-independent during the localization in that reference is made to the centre of the point-symmetric and rotationally asymmetric diffraction image of each isolated fluorescence emitter. The position of the centre provides the localization result.

The spectrally selective element may have various designs. A simple possibility is a plate made of a dispersive material the thickness of which varies along a circle about an optical axis. Naturally, instead, of utilizing the dispersion of the material and thus varying the thickness, the transmission property can also vary in general.

A particularly advantageous embodiment realizes the spectrally selective element as a plate made of several wedge-shaped sectors which differ in respect of their spectral transmission properties. If sectors lying point-symmetric relative to each other are then provided with identical spectral transmission properties, the already mentioned advantageous rotationally symmetric image is obtained for each individual isolated fluorescence molecule. The centre of symmetry of the plate is at the same time the penetration point of the optical axis.

The localization can be made easier if the spectrally selective element has a central area lying on the optical axis which central area has broadband spectral transmission properties and is surrounded by sectors which differ from each other and preferably also from the central area in respect of their spectral transmission properties. In the central area, the diffraction-limited point image of each fluorescence emitter is then spectrally independent, which allows for a simple localization. Through the sectors, each diffraction-limited point image has at least one ear, preferably two ears lying symmetric relative to each other, the position of which encode(s) the colour emission.

The optical structure of the microscope is particularly simple if the spectrally selective element is arranged in a pupil or close to a pupil of the imaging beam path.

With a spectrally selective element which has a point-symmetric variation of the transmission properties, one obtains diffraction-limited point images for the fluorescence emitters which images have the shape of a bow tie. The rotation position of the bow tie encodes the colour in which an isolated emitter luminated.

It is understood that the features mentioned above and those yet to be explained below can be used, not only in the stated combinations, but also in other combinations or alone, without departing from the spirit or scope of the present invention. Where method features are mentioned in this description, they are realized in operation of the microscope by a correspondingly designed control device. A disclosure of functional features of the control device also applies analogously as a description of corresponding method features, e.g. steps.

The invention is explained in further detail below by way of example with reference to the attached drawings which also disclose features essential to the invention. There are shown in:

DESCRIPTION OF THE FIGURES

FIG. 1 a schematic representation of a microscope for wavelength-selective, high-resolving fluorescence microscopy, FIG. 2 a schematic top view of a spectrally selective element in the microscope of FIG. 1, FIG. 3 a detail from a frame which was produced with the microscope of FIG. 1, wherein the detail shows exemplary diffraction-limited images of an isolated fluorescence emitter, FIG. 4 a frame with several images according to FIG. 3, FIG. 5 a representation similar to FIG. 2 for an embodiment having a modified spectrally selective element, FIG. 6 a diagram for illustrating the spectral properties of different areas of the spectrally selective element of FIG. 5, FIG. 7 a representation similar to FIG. 3 for the embodiment comprising the element of FIG. 5 and FIG. 8 a fluorescence microscope according to the state of the art with several colour channels.

DETAILED DESCRIPTION

Figure 8:
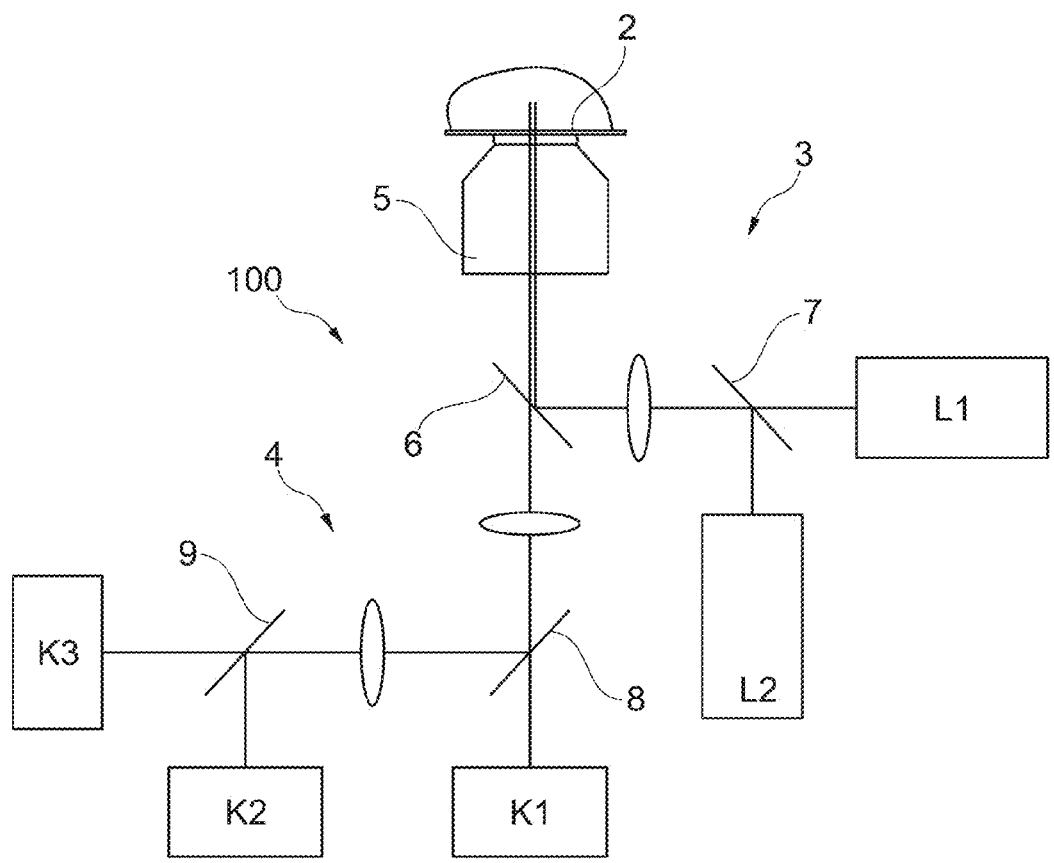

FIG. 1 schematically shows a fluorescence microscope 1 the operation of which is controlled by a control device C. The control device is connected to the elements of the microscope 1 via connections that are not shown, in particular to laser source(s) and camera. Elements or components which correspond functionally and/or structurally to elements or components which have already been explained with reference to the microscope 100 of FIG. 8, thus in respect of their function or structure correspond to the state of the art, are provided with the same reference numbers in the representation of FIG. 1. Their description therefore need not be repeated.

The microscope 1 of FIG. 1 comprises, in addition to the illumination beam path 3, an imaging beam path 10 which, however, as will be explained later, functions without spectral division into several colour channels. Therefore, only a single camera K1 is required. The imaging of the specimen is guided through a spectrally selective element 11 which modifies the point-spread function of the microscope 1 to be rotational asymmetric. As the microscope 1 otherwise records diffraction-limited images of the isolated fluorescence molecules, these images are now modified by the spectrally selective element 1 to be asymmetric in respect of the point-spread function.

FIG. 2 schematically shows a simplified top view of the spectrally selective element 11 along the optical axis which is thus perpendicular to the drawing plane in the representation of FIG. 2. The spectrally selective element 11 comprises for example four sectors 12, 13, 14 and 15 which have different spectral transmission characteristics. The sectors differ in respect of their spectral filter properties, wherein sectors lying opposite each other in the represented example have identical spectral filter properties, but neighbouring sectors differ in their filter properties. By way of example and without limitation for the principle of the invention, opposite sectors are provided with identical transmission properties. Sectors 12 and 13 have identical spectral transmission properties. This applies analogously to sectors 14 and 15.

FIG. 3, which represents a detail of a frame 16 which is produced with the microscope 1, shows the effect of the spectrally selective element 11 on a point image of an isolated emitter. The spectrally selective element 11 deforms the point-spread function of an individual illuminated fluorophore rotationally asymmetrically, namely in the shape of the bow tie represented in FIG. 3. FIG. 3 shows a detail of a frame 16, which is obtained with the microscope 1 when the PALM method is carried out under control of the control device C, if a fluorophore luminates isolated. Depending on the wavelength at which the fluorophore primarily illuminates, the radiation of this fluorophore is transmitted either by the sectors 12 and 13 or the sectors 14 and 15. Correspondingly a a bow tie 17a or 17b forms. The rotation position of the bow tie 17 about a centre 18 encodes the colour of the luminating fluorophore. Two bow ties 17a and 17b for different fluorescent colours are shown schematically in FIG. 3. Naturally, the transmission properties of the sectors of the spectrally selective element 11 are chosen such that for a given application only one of the two bow ties 17a or 17b is present. The direction of the main axis of the bow tie is evaluated by the control device C, which direction provides an indication of the wavelength at which the fluorophore laminates. The centre 18 is the starting point for the localization of the fluorophore which follows the known PALM approaches which have already been explained above with reference to the term "superresolution".

The bow tie 17a is present if the radiation of the emitter is such that the radiation was transmitted by the sectors 12 and 13 (and blocked by the sectors 14 and 15). The bow tie 17b occurs if the wavelength of the fluorescence emitter was transmitted only by the sectors 14 and 15. The bow ties 17a and 17b have the centre 18 which corresponds to the actual position of the fluorescence emitter. By determining the centre 18 of the bow tie 17a or 17b the position of the fluorescence emitter can thus be specified with a precision better than the spatial resolution. The angular position of the bow tie 17a or 17b yields the colour indication.

The use of the spectrally selective element and only one colour channel in the imaging beam path has the advantage that only one of the comparatively expensive cameras is needed. The outlay on construction and the space requirement associated with several cameras are also no longer necessary. Finally, the frames 16 are also automatically aligned in respect of the colour channels, as all emitters are recorded in a single image, independent of their colour. A chromatic aberration due to a misalignment of individual colour channels is thus avoided in principle by the structure. The obtained images are inherently chromatically defect-free in this respect.

The operation of the microscope is controlled by the control device C. Where method features are described above or below, the control device C ensures that the microscope 1 is set into a corresponding mode of operation which realizes such method features.

Naturally, the design of the spectrally selective element 11, as represented in FIG. 2, is purely exemplary. The spectrally selective element 1 need not necessarily be formed from sectors. The only decisive factor is that its transmission properties are such that for an individual luminating fluorophore the point-spread function is asymmetrically distorted depending on the spectral range and/or the central wavelength, etc. at which the fluorophore luminates. From the asymmetry the control device C can then easily derive a colour indication for the fluorophore.

A point-symmetric configuration of the spectral transmission properties of the spectrally selective element 11, as in FIG. 2, has the advantage that the centre of each point-spread image of an individual laminating fluorophore can easily be used to localize the fluorophore.

The use of sectors that are largely constant in respect of their transmission properties and are separated from each other further has the advantage that when the method is carried out the control device C only needs to distinguish between a discrete number of rotationally asymmetric distortions. The price for this simplification is that only particular colours or spectral ranges can be distinguished.

It is likewise possible to configure the transmission properties of the spectrally selective element such that the rotationally asymmetric spectral distortion changes in a plurality of fine stages or even continuously with the wavelength. For the price of a thereby, more precise determination of the rotational asymmetry of the point-spread images becoming necessary in each frame, a higher spectral resolution of the colour indication of the fluorophores is obtained.

Figure 4:
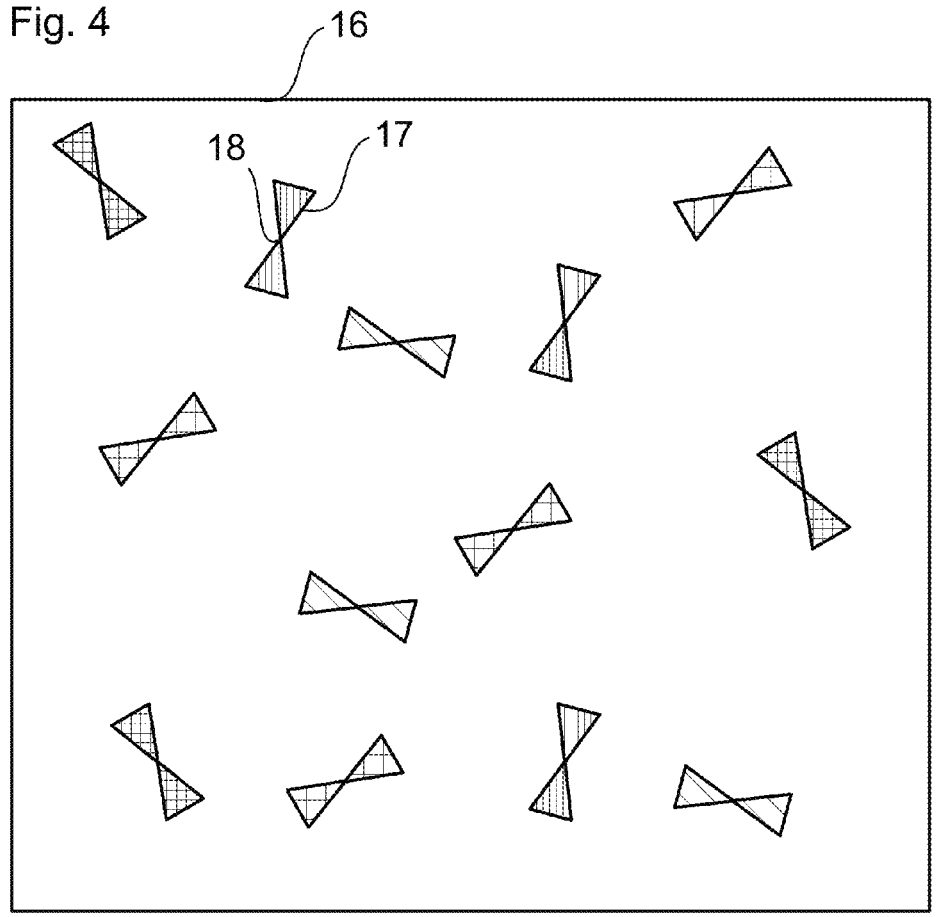

FIG. 4 shows by way of example a frame 16 which is obtained with the microscope 1 under the control of the control device C, which frame was produced with a spectrally selective element 11 which produces four different discrete rotational asymmetries for four different colours of luminating fluorescence emitters. Compared with the element represented in FIG. 2, the spectrally selective element 11 with which the frame 16 of FIG. 4 was produced has, not only two sectors lying opposite each other in pairs, but four pairs—thus eight sectors in total. The point-symmetric design of the spectrally selective element 11 ensures that the point-spread image of an individual fluorophore is a bow tie 17 again. In the frame 16 there are four different rotation positions encoding the four different transmission bands of the spectrally selective element. The centres 18 again serve to localize the fluorophores.

As the frame of FIG. 4 clearly shows, all colour channels are contained in a single frame 16. The problem of a chromatic aberration because of an incomplete alignment of several independently recorded colour channels thus does not arise. The number of frames also does not increase linearly with the number of colour channels.

Figure 5:
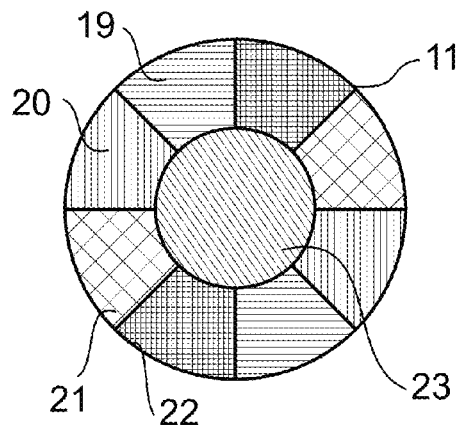
Figure 6:
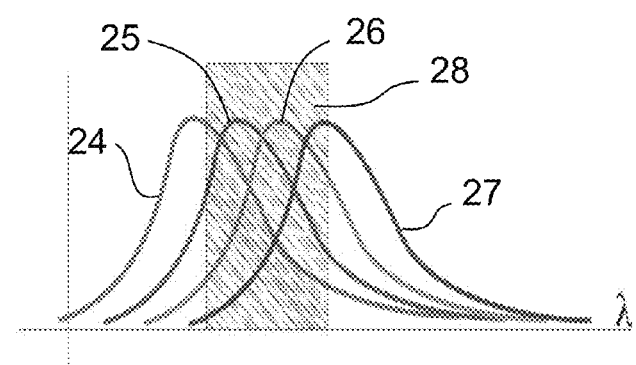
Figure 7:
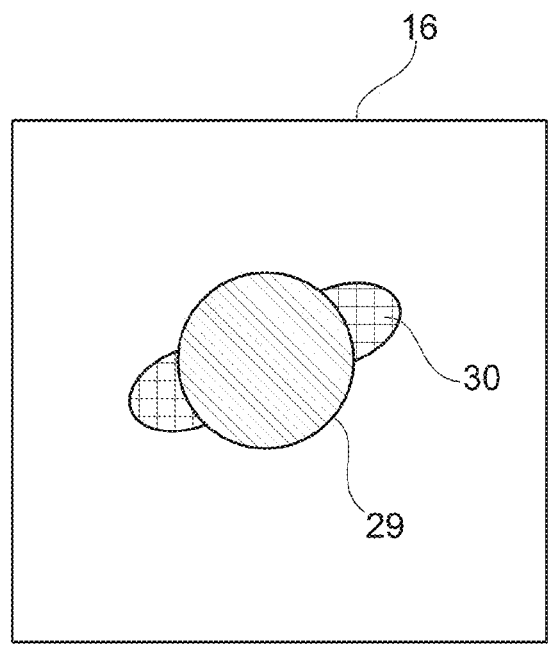

FIG. 5 shows a top view similar to FIG. 2. However, the spectrally selective element 11 here is formed not only by four sector pairs 19, 20, 21 and 22 (as were used for the frame 16 of FIG. 4), but the spectrally selective element 11 also comprises a central area 23 transmitting in broadband. The spectral filter properties are plotted by way of example in FIG. 6, which shows the transmission through the respective area as a function of the wavelength $\lambda$. Transmission curve 24 is allocated to the sector pair 19, transmission curve 25 to the sector pair 20, transmission curve 26 to the sector pair 21 and transmission curve 27 to the sector pair 22. The central area 23 transmits in broadband in the spectral range 28. An image of a fluorophore is then, as represented in FIG. 7, which shows a detail of a frame 16, formed as a circular spot 29 with ears 30. The rotation position of the ears 30 encodes the colour information. The central spot 29 makes it easier to localize the fluorophore in the frame 16, i.e. to obtain the so-called superresolution. The structure of the spectrally selective element 11 is thus modified compared to the design principle of the spectrally selective element 11 of FIG. 2 to the effect that localization of the fluorophores is made easier.

As becomes clear from the above description, the spectrally selective element effects a rotational asymmetry of the point-spread function of an individual luminating fluorophore depending on the spectral composition of the fluorescence radiation. It is therefore advantageous to provide a changing mechanism for the spectrally selective element 1 in order to tune the spectral transmission characteristics, for example the transmission characteristics of individual sectors, to a microscopy application, in particular to fluorophores used.

The above-described point-symmetric rotationally asymmetric point-spread functions make it easier to localize the molecule. However, this is not essential. Thus it is possible at any time to abandon the point symmetry of the transmission properties of the spectrally selective element 11, as the localization can be carried out simply using, the spot 29. If a central area 23 is used, the point-spread image of a fluorophore then would have, not two ears 29, but only one ear. Such an approach increases the spectral resolution by a factor of 2. A configuration of the transmission properties of the spectrally selective element 11 that is not point-symmetric can also be realized, without a central area 23. It is only essential that during the evaluation of the frames 16 the basic structure of the spectrally dependent rotational asymmetry is known, in order that localization can be carried out easily by the recognition of the rotationally asymmetric image of the fluorophore. For this, it is only necessary to know how the rotationally asymmetric point-spread image lies relative to the respective centre at which the fluorophore is to be expected.

The invention claimed is:

1. A method for wavelength-selective and high spatial resolving fluorescence microscopy, comprising:
   a) Repeatedly exciting fluorescence emitters in a specimen to emit fluorescence radiation and producing frames of the specimen with a microscope having an imaging beam path with an optical resolution, where in the fluorescence emitters are excited to emit fluorescence radiation such that at least a sub-set of the fluorescence emitters is isolated in each frame,
   b) Localizing the positions of the isolated fluorescence emitters in produced frames with a localization precision exceeding the optical resolution, and producing a high resolution complete image therefrom,
   c) wherein the imaging beam path of the microscope has a spectrally selective element during the production of the frames and further comprising generating a spectrally dependent rotational asymmetric point-spread function, with the result that images of isolated fluorescence emitters have a rotational asymmetry which depends on a wavelength at which the isolated fluorescence emitters fluoresce, and
   d) analyzing, in the frames the images of the isolated fluorescence emitters with respect to rotational asymmetry and deriving an indication of the wavelength of the isolated fluorescence emitters therefrom.

2. The method according to claim 1, further comprising in step c) generating by the rotational asymmetry a rotational position of each image of one of the isolated fluorescence emitters which rotational position depends on the wavelength at which the isolated fluorescence emitter fluoresce.

3. The method according to claim 1, wherein step d) further comprises determining an angle indication for each image of one of the isolated fluorescence emitters and deriving the indication of the wavelength of the isolated fluorescence emitters from the angle indication.

4. The method according to claim 1, wherein in step c) the spectrally selective element gives a point-symmetric rotational asymmetry to the point-spread function.

5. The method according to claim 4, wherein step d) further comprises determining a rotation position of the image for each image of one of the isolated fluorescence emitters and deriving the indication of the wavelength of the isolated fluorescence emitters from the rotation position.

6. The method according to claim 4, further comprising determining a center for each isolated fluorescence emitter in the image and in step b) using the center for determining the position of the isolated fluorescence emitters.

7. A fluorescence microscope for wavelength-selective imaging of a specimen with a spatial resolution better than an optical resolution, the microscope comprising:
   an illumination device which is designed to repeatedly excite fluorescence emitters to emit fluorescence radiation in the specimen,
   an imaging device, comprising an imaging beam path, which is designed to produce frames of the specimen with the optical resolution,
   a control device which is designed to control the illumination device and the imaging device such that several frames of the specimen are produced, wherein the fluorescence emitters are excited to emit fluorescence radiation such that at least a sub-set of the fluorescence emitters is isolated in each frame, wherein
   the control device is designed to localize in the produced frames the positions of the isolated fluorescence emitters with a localization precision exceeding the optical resolution and to produce a high-resolution complete image therefrom,
   the imaging beam path of the microscope has a spectrally selective element which, during the production of the frames, generates a spectrally dependent rotational asymmetric point-spread function, with a result that images of isolated fluorescence emitters have a rotational asymmetry which depends on a wavelength at which the isolated fluorescence emitters fluoresce, and
   the control device is designed to analyse, in the frames the images of the isolated fluorescence emitters with respect to their rotational asymmetry and to derive therefrom an indication of the wavelength of the isolated fluorescence emitters.

8. The fluorescence microscope according to claim 7, wherein the spectrally selective element is formed as a plate made of a dispersive material the thickness of which varies along a radius about an optical axis.

9. The fluorescence microscope according to claim 7, wherein the plate is constructed from several wedge-shaped sectors which differ in respect of their spectral transmission properties.

10. The fluorescence microscope according to claim 7, wherein the spectrally selective element has a central area, lying on an optical axis, which is surrounded by the sectors which differ from each other.

11. The fluorescence microscope according to claim 7, wherein the spectrally selective element is arranged in a pupil or close to a pupil of the imaging beam path.

12. The method according to claim 5, determining a center for each isolated fluorescence emitter in the image and using the center in step b) to determine the position of the isolated fluorescence emitters.

13. The fluorescence microscope according to claim 8, wherein the plate is constructed from several wedge-shaped sectors which differ in respect of their spectral transmission properties, wherein preferably sectors lying point-symmetric relative to each other have identical spectral transmission properties.

14. The fluorescence microscope according to claim 8, wherein the spectrally selective element is arranged in a pupil or close to a pupil of the imaging beam path.

15. The fluorescence microscope according to claim 9, wherein the spectrally selective element is arranged in a pupil or close to a pupil of the imaging beam path.

16. The fluorescence microscope according to claim 10, wherein the spectrally selective element is arranged in a pupil or close to a pupil of the imaging beam path.

17. The fluorescence microscope according to claim 9, wherein sectors lying point-symmetric relative to each other have identical spectral transmission properties.

18. The fluorescence microscope according to claim 10, wherein the sectors surrounding the central area also differ from the central area in respect of their spectral transmission properties.

\* \* \* \* \*

UNITED STATES PATENT AND TRADEMARK OFFICE
CERTIFICATE OF CORRECTION

PATENT NO. : 9,091,653 B2  
APPLICATION NO. : 13/754679  
DATED : July 28, 2015  
INVENTOR(S) : Thomas Kalkbrenner et al.

Page 1 of 1

It is certified that error appears in the above-identified patent and that said Letters Patent is hereby corrected as shown below:

In the Specification

Col. 1, line 36, delete "result," and insert --result--

Col. 1, line 40, delete "so"

Col. 2, line 22, delete "is" and insert --a--

Col. 2, line 24, delete "an" and insert --art--

Col. 2, line 44, delete "as" and insert --a--

Col. 2, line 58, delete "space," and insert --space. A--

Signed and Sealed this  
Twelfth Day of January, 2016

Michelle K. Lee  
*Director of the United States Patent and Trademark Office*